US00PP14935P2

(12) United States Plant Patent
Clark

(10) Patent No.: US PP14,935 P2
(45) Date of Patent: Jun. 22, 2004

(54) BLACKBERRY PLANT NAMED 'CLARK GOLD'

(50) Latin Name: *Rubus trivialis*
Varietal Denomination: Clark Gold

(76) Inventor: John William Clark, P.O. Box 477, County Rd. 476, Palacios, TX (US) 77465

( * ) Notice: Subject to any disclaimer, the term of this patent is extended or adjusted under 35 U.S.C. 154(b) by 75 days.

(21) Appl. No.: 10/180,641

(22) Filed: Jun. 24, 2002

(51) Int. Cl.[7] ..... A01H 5/00

(52) U.S. Cl. ..... Plt./203

(58) Field of Search ..... Plt./203

*Primary Examiner*—Anne Marie Grunberg

(57) ABSTRACT

A new and distinct variety of blackberry plant lacking anthocyanin coloration in it's various plant parts and having yellow fruit is described. The new variety named 'Clark Gold' also has double flowers and enlarged sepals. 'Clark Gold' is a sport of the southern dewberry, *Rubus trivalis*, and is a biennial, thorny, trailing-vine plant type. The yellow fruit is of medium size and has the sweetness of its wild blackberry relative. It is also a very early variety with low chill requirements.

6 Drawing Sheets

*Rubus trivialis*; Variety 'Clark Gold'.

BACKGROUND OF THE VARIETY

This new variety named 'Clark Gold' is the result of a spontaneous mutation of the southern dewberry, *Rubus trivialis*, a wild blackberry species, and was discovered on cultivated land in south Texas (Jackson County). The plants of the new variety lack anthocyanin pigment throughout all tissues, including the fruit, which is yellow at maturity, unlike the dark purple fruit of normal blackberries. This variety like most blackberry cultivars has biennial canes with a dormant period between first year canes primocanes) and second year canes (floricanes) prior to flowering and fruiting. This new variety is analogous to 'Kiwigold', U.S. Plant Pat. No. 11,313, a yellow-fruited mutation of the red raspberry variety 'Heritage', although occurring in a blackberry species rather than a raspberry species.

Blackberry and raspberry species belong to the same genus Rubus, but fall within different subgenera. The distinguishing morphological difference between blackberries and raspberries is evident when the fruit is picked. In the blackberry the central receptacle (torus) of the fruit remains intact with the fruit when picked, whereas in the raspberry the torus remains attached to the stem resulting in a fruit with a hollow core. In this respect, 'Clark Gold' is a typical blackberry fruit with a solid core when picked. There are commercial raspberry varieties available with yellow fruit, as well as those with red or black fruit. To date there are no commercial varieties of blackberry with yellow fruit.

This new cultivar is intended to be marketed as a novel blackberry variety for home and commercial blackberry fruit production. The fruit in turn can be used for fresh eating or as processed fruit or juice. This variety could also be used as a parent in a plant breeding program to transfer the yellow fruit character and the associated lack of anthocyanin to other blackberry cultivars. The absence of anthocyanin is, in effect, a gene marker for the yellow fruit character and will facilitate selection for yellow fruit in a hybridization program. The absence of anthocyanin can be detected at a very early stage of the primocane (first year) while the yellow fruit color is not evident until maturity of the fruit in the floricane (second year).

SUMMARY OF THE INVENTION

The present invention relates to a new and distinct variety of blackberry plant having a yellow fruit and lacking anthocyanin in its various plant parts. This new variety also has double flowers and large, elongated sepals which distinguish it from the wild dewberry, *Rubus trivialis*, from which it derives. The original plant was a naturally occurring whole plant mutation found in a fencerow along County Road 476 in Jackson County, Tex. The fencerow was bordering a cultivated field, which had been planted at various times to different crops including pasture grasses, grain sorghum and various varieties of blackberries.

The original plant of the new variety was propagated asexually by tip layering in 2000 and 2001. All new plants were phenotypically stable for yellow fruit and the absence of anthocyanin. The asexual reproduction occurred at the same location in Jackson County, Tex.

This new variety has not been observed under environmental conditions outside of southern Texas. The phenotype may vary considerably in other environments, particularly in more northerly climes, although the yellow fruit color and absence of anthocyanin should not be affected.

The new cultivar 'Clark Gold' has three distinctive characteristics which distinguish it from its progenitor, the southern dewberry, *Rubus trivialis*, and other blackberry varieties. One of these is major and readily visible (yellow fruit and yellow green plant), while the other two are variations in the floral structure. 'Clark Gold' is a spontaneous genetic mutation in which normal anthocyanin pigmentation is suppressed, resulting in vegetative tissues which lack red and purple pigments, and in the fruit which is yellow at maturity. The absence of anthocyanin and the yellow fruit are presumed to be different expressions in the vegetative and fruit tissues, respectively, of the same genetic trait-ie. suppressed anthocyanin production. The variations in the floral structure of the new variety are 1) double flower which has an increase in the number of petals over the normal corolla complement of five and 2) larger and elongated sepals as compared to the normal calyx. The petals of the new variety are also larger, which combined with the increased petal number, give the flower a fuller appearance, thus the term "double flower". These floral abnormalities appear to be genetic traits and not symptoms of the Rosette disease, also known as "double blossom", caused by the fungal pathogen *Cercosperella rubi*, because 'Clark Gold' flowers produced fruit of normal size and drupelet number unlike Rosette flowers which are sterile.

Like the wild dewberry, *Rubus trivialis*, from which it derives 'Clark Gold' is a trailing vine with numerous curved thorns on the canes, petioles and petiolules. The wild dewberry (WDB) has normal anthocyanin coloration which shows in nearly all its plant tissues as a reddish tinge of varying intensity in the canes, leaves, petioles, petiolules and thorns. By contrast, 'Clark Gold' plants lack anthocyanin and its vegetation is a light green color to yellow green color with no trace of red coloration. The primocanes of 'Clark Gold' are in the Yellow Green Group (146C) of The Royal Horticultural Society Colour Chart while WDB primocanes are in the Red Purple Group (59A). Anthocyanin coloration in normal plants is especially pronounced in winter foliage, and around leaf margins, at the base of petioles and in damaged plant tissues. The fruit of normal blackberries turn from green to bright red to dark purple or "black" at maturity. 'Clark Gold' berries are dark green when immature and turn to yellow, Yellow Group (12B) as they ripen without passing through the red berry stage.

*Rubus trivialis*, like most blackberry cultivars, has the normal corolla complement of 5 petals, which are discrete and spatulate (club-shaped). In contrast, 'Clark Gold' flowers usually have 6 or more petals, and as many as 15 petals. The petals are also larger, fan-shaped and overlapping. Normal blackberry flowers also have a small calyx with 5 sepals. 'Clark Gold' flowers have a larger calyx with elongated sepals. In all other aspects 'Clark Gold' is morphologically identical to its progenitor, *Rubus trivialis*, including fruit characteristics such as size, shape, pH (3.26) and soluble solids (8.7%).

BRIEF DESCRIPTION OF ILLUSTRATIONS

DETAILED DESCRIPTION OF THE NEW VARIETY

Figure 1:
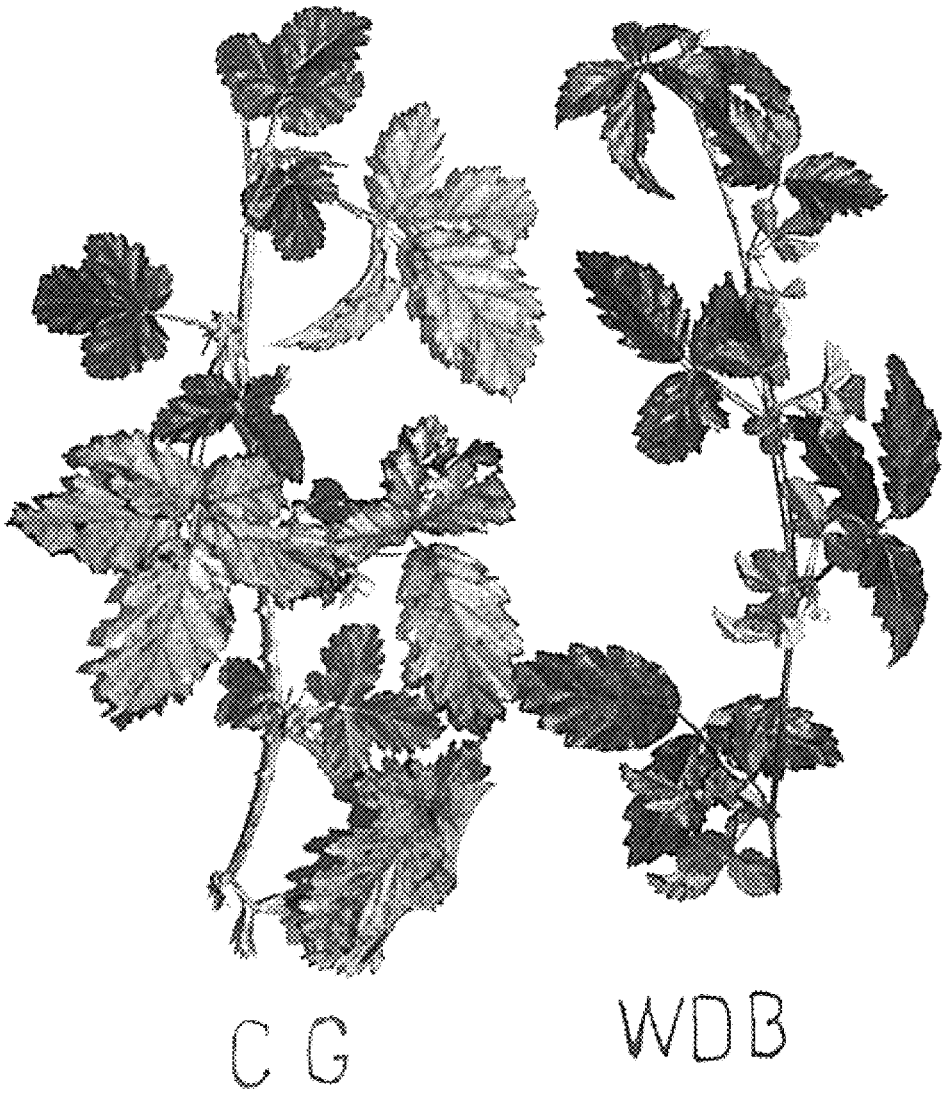
FIG. 1 shows winter foliage of 'Clark Gold' (CG) and *Rubus trivialis*, the wild dewberry(WDB).
Figure 2:
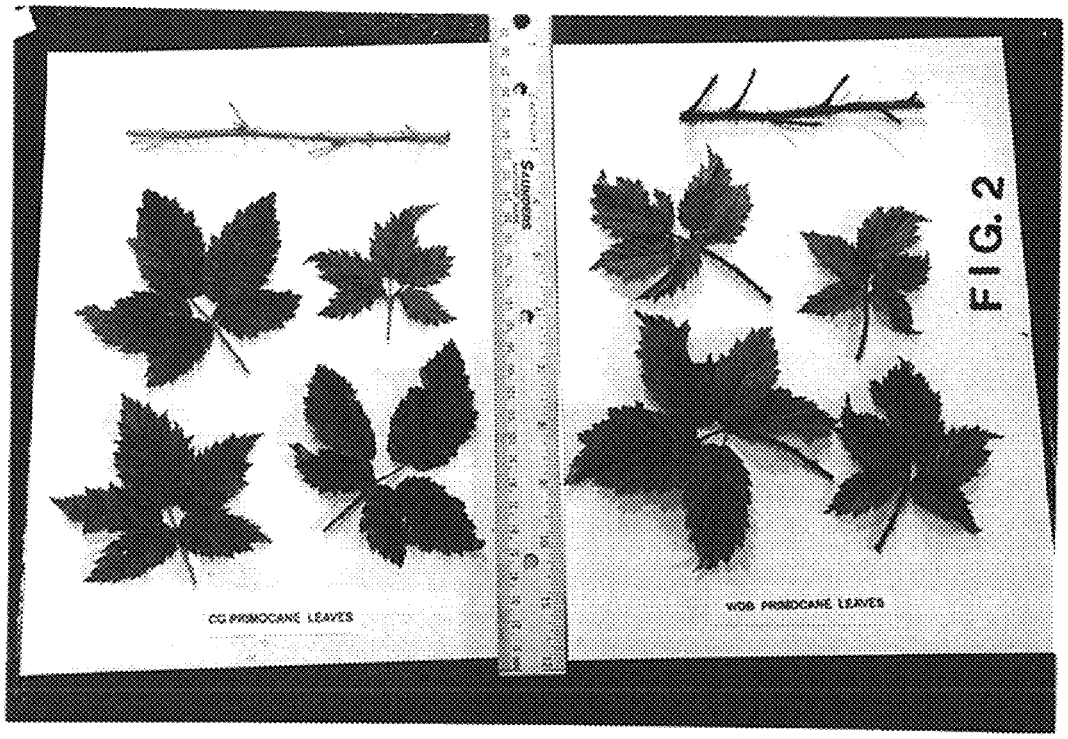
FIG. 2 shows primocane leaves (5-foliate) of 'Clark Gold' (CG) and *Rubus trivialis*, the wild dewberry (WDB).
Figure 3:
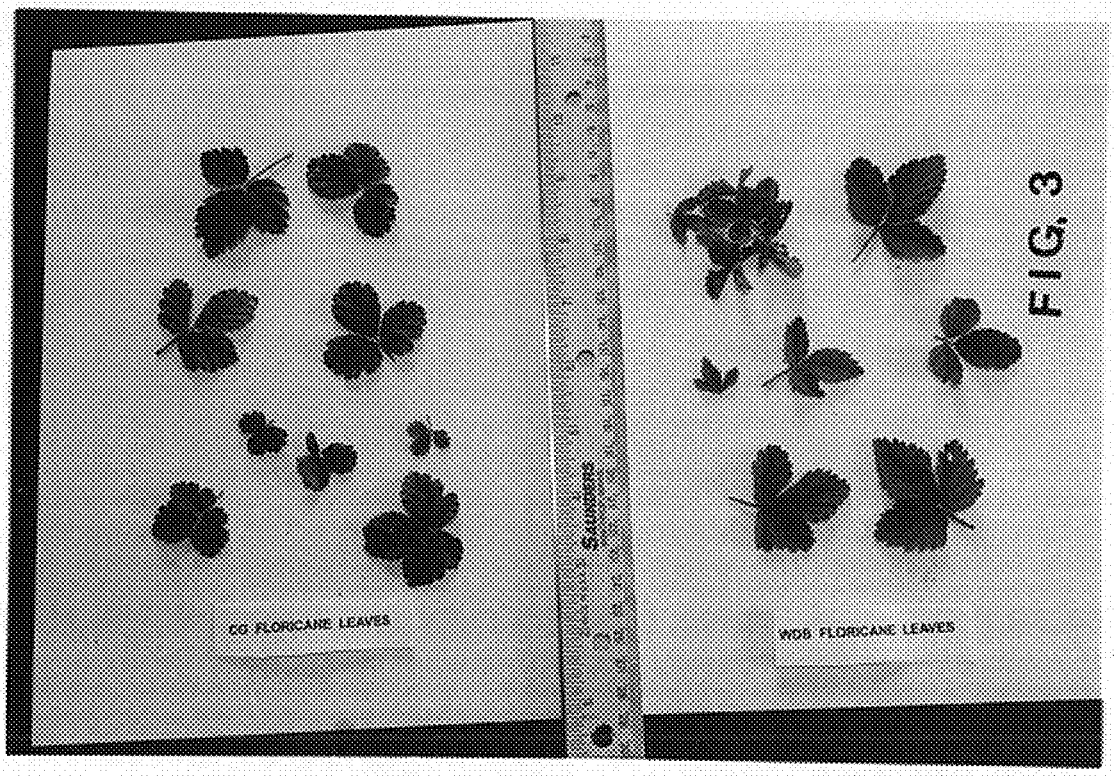
FIG. 3 shows floricane leaves (3-foliate) of 'Clark Gold' (CG) and *Rubus trivialis*, the wild dewberry (WDB).
Figure 4:
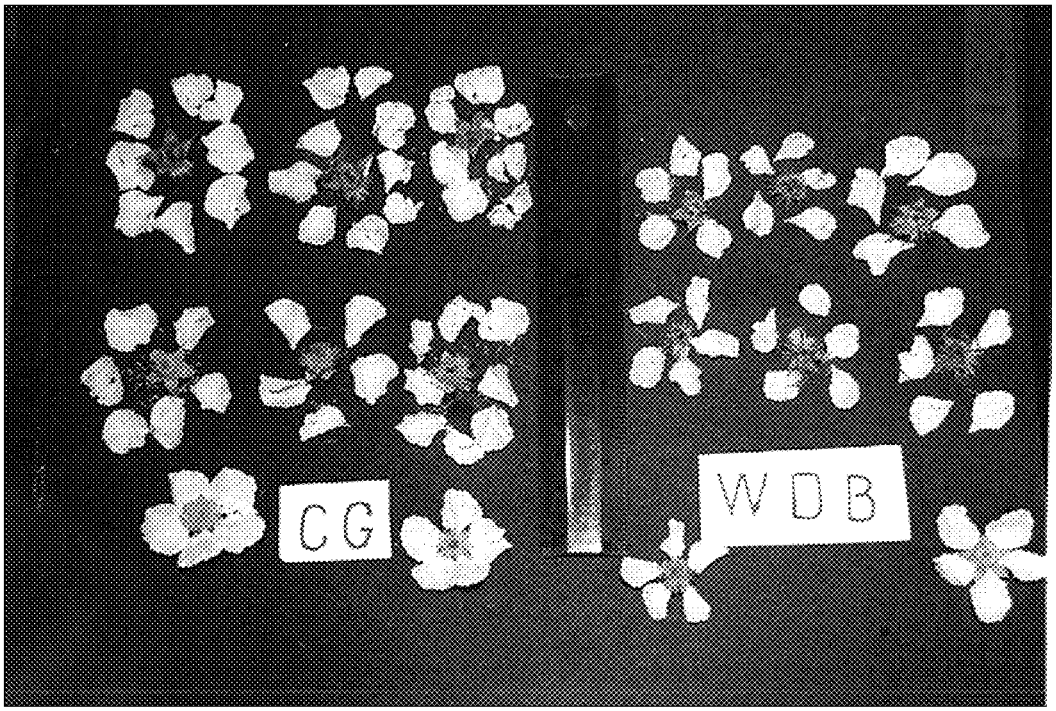
FIG. 4 shows flowers and petal numbers of flowers of 'Clark Gold' (CG) and *Rubus trivialis*, the wild dewberry (WDB).
Figure 5:
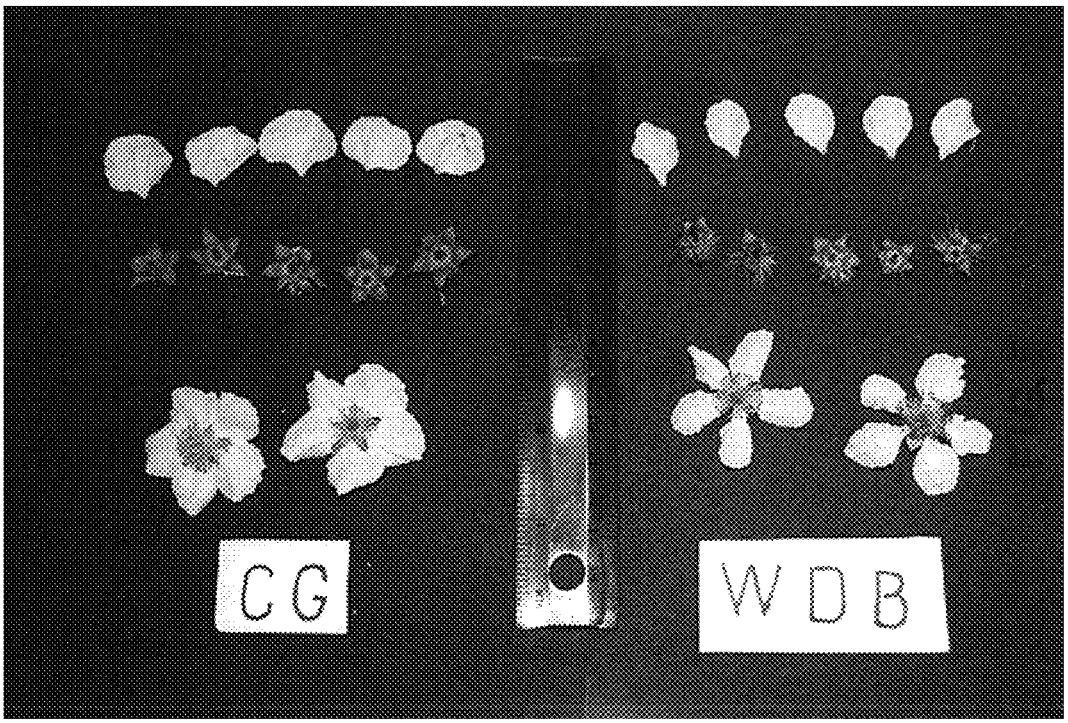
FIG. 5 shows shape and size of flowers and calyx of 'Clark Gold' (CG) and *Rubus trivialis*, the wild dewberry (WDB).
Figure 6:
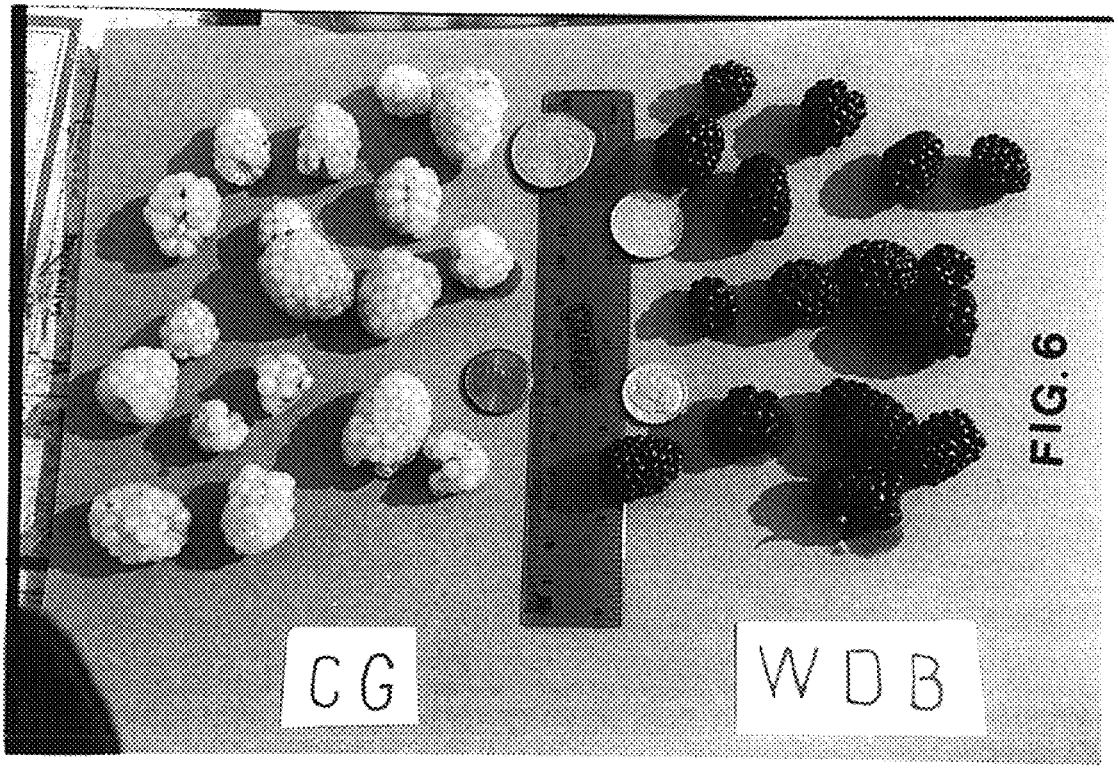
FIG. 6 shows yellow fruit of 'Clark Gold' (CG) and normal black fruit of *Rubus trivialis*, the wild dewberry (WDB).

The descriptions reported herein are from specimens grown in Jackson County, Tex. Color data are presented in Royal Horticultural Society (R.H.S.) Colour Chart designations. Where dimensions, sizes, colors, and other characteristics are given, it is to be understood that such characteristics are approximations of averages set forth as accurately as practicable.

Plant:

*Size*.—Medium, trailing vine with a dense array of thorns.

*Growth habit*.—Vigorous, sprawling vine forming mats or mounds and scrambling in bushes and fences.

*Canes*.—Long-running, thorny and glandular hairy. Cane internode length at midpoint: 3.87 cm.

*Primocane*.—Diameter at midpoint: 3 to 5 mm. Color: Yellow Green Group (146C). Thorn length: 4 to 5 mm. Thorn color — Yellow-Green Group (144A).

*Floricane* (*wintercane*).—Diameter at midpoint: 2 to 3 mm. Thorn length: 2 to 3 mm. Floricane and thorn color — Yellow-Green Group (146B).

Foliage:

*Primocane*.—Leaves — Medium. Mature compound leaf length 8.6 cm; width 8.9 cm. Leaflet: length 4.3 cm; width 2.1 cm; shape narrow-elliptic with acute apex and base; margin incised; abaxial and adaxial surfaces glabrous. Color of adaxial leaflet surface Yellow Green Group (137A); abaxial surface Yellow Green Group (137C). Number of leaflets per compound leaf: 5. Petiole length: 3.2 cm. Petiolule length: 4 to 8 mm. Stipule length: 5 to 7 mm. Color of petiole and petiolule Yellow Green Group (146D). Leaf midvein color — Green Group (137A); petiole, petiolule end stipule color — Yellow-Green Group (146C).

*Floricane*.—Leaves — Small to very small. Mature compound leaf length 4.2 cm; width 4.1 cm. Leaflet: length 1.9 cm; width 1.3 cm; shape elliptic with acute apex, laterals also with a single basal lobe; margin incised; glabrous abaxial and adaxial surfaces. Color of adaxial leaflet surface Yellow Green Group (137A); abaxial surface Yellow Green Group (137C). Number of leaflets per compound leaf: 3. Petiole length 1.4 cm. Petiolule length: 2 mm. Stipule length: 2 to 4 mm. Leaf midvein color — Green Group (137B); petiole, petiolule and stipule color — Yellow-Green Group (146B).

*Flowers*.—Mostly solitary on erect peduncles, occasionally 2 or 3 on branched peduncle.

*Date of bloom*.—First — Julian 75: 50% — Julian 84; Last — Julian 110.

*Blossom color*.—White. Petal color — White Group (155D).

*Reproductive organs*.—Stamens — erect, numerous. Pistils — numerous. Pollen — normal. Stamen color — Yellow-Green Group (153A); stigma color — Yellow-Green Group (151D).

*Flower diameter*.—3.4 cm.

*Petal size*.—Length — 1.7 cm. Width — 1.9 cm.

*Number of petals per flower*.—5 to 15, most commonly 7 to 10.

*Calyx*.—Sepals elongated, apex bluntly serrated. Diameter — 1.9 cm. Sepal color — Green Group (137A).

*Peduncle length*.—5.2 cm. Peduncle color — Yellow-Green Group (146B).

Fruit:

*Maturity*.—Very early, 10 to 15 days before 'Brazos' (non-patented). Average first ripe date is April 19. Average period of ripening is April 19 to May 7.

*Size*.—Medium, average 3.7 g. Length — 2.4 cm. Diameter at base — 1.8 cm.

*Shape*.—Blocky-ovoid, occasionally spheroid.

*Color*.—Yellow Group (12B).

*Seed size*.—Small, 2.4 mg/seed. Seed color — Yellow-Orange Group (18C).

*Soluble solids*.—8.7%.

*pH*.—3.28 (as measured by pH meter on a sample of 20 ripe berries).

*The variety*.—The most distinctive features of the variety are the yellow fruit and the absence of anthocyanin in the various plant tissues. Both primocanes and floricanes are thorny, trailing-vine plant types. The medium-sized fruit has the same sweetness as its wild dewberry relative, *Rubus trivialis*. Originating in USDA hardiness zone 9, 'Clark Gold' is an early ripening, very low chill variety.

I claim:

1. A new and distinctive variety of blackberry plant, substantially as described and illustrated herein, characterized by (A) having yellow fruit and the absence of anthocyanin coloration in the vegetative and floral parts, (B) double flowers and (C) elongated sepals.

* * * * *

CG
WDB

CG
WDB